US00PP26521P3

(12) United States Plant Patent
Danziger

(10) Patent No.: US PP26,521 P3
(45) Date of Patent: Mar. 15, 2016

(54) ***SUTERA* PLANT NAMED 'DANCOP102'**

(50) Latin Name: *Sutera cordata*
Varietal Denomination: DANCOP102

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 104 days.

(21) Appl. No.: 14/120,180

(22) Filed: May 2, 2014

(65) Prior Publication Data

US 2015/0319906 P1 Nov. 5, 2015

(51) Int. Cl.
*A01H 5/02* (2006.01)

(52) U.S. Cl.
USPC ..... Plt./485

(58) Field of Classification Search
USPC ..... Plt./485
See application file for complete search history.

*Primary Examiner* — Susan McCormick Ewoldt
(74) *Attorney, Agent, or Firm* — Cassandra Bright

(57) ABSTRACT

A new and distinct *Sutera* cultivar named 'DANCOP102' is disclosed, characterized by early and abundant extra large white flowers, a semi-trailing elongated habit, very well branched plant habit with long, strong branches and strong vigor. The new variety is a *Sutera*, normally produced as an outdoor garden or container plant.

2 Drawing Sheets

Figure 1:
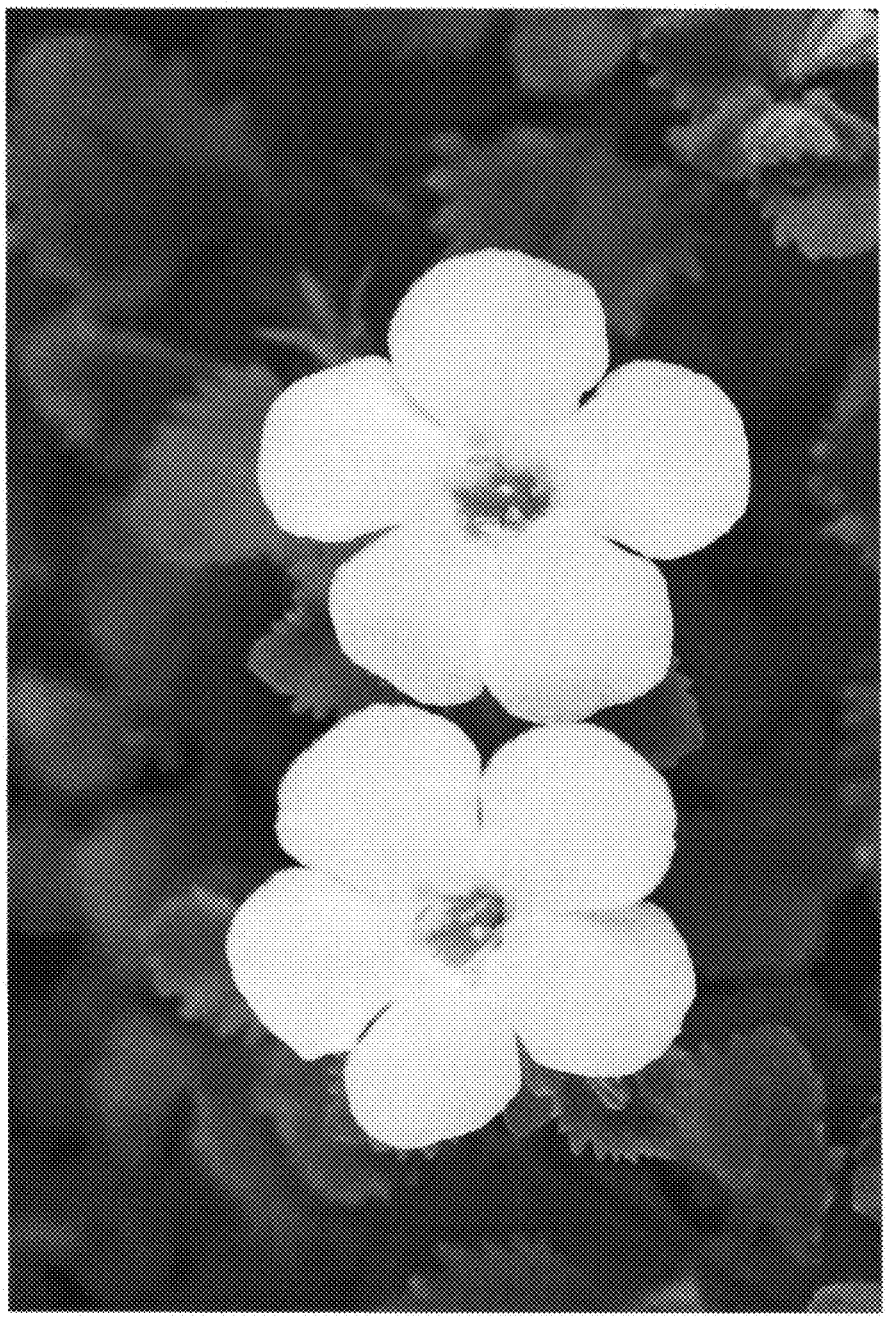

Latin name of the genus and species: *Sutera cordata.*
Variety denomination: 'DANCOP102'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The open pollination resulting in this new variety was made during January of 2010.

The seed parent is the unpatented, proprietary seedling variety referred to as *Sutera cordata* 'cv. 09-1472' The pollen parent is unknown as it was an open pollination breeding program. The new variety was discovered in July of 2010 by the inventor in a group of seedlings resulting from the 2010 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during August of 2010 and has shown that the unique features of this cultivar are stable and reproduced true to type in more than 20 successive generations.

SUMMARY OF THE INVENTION

The cultivar 'DANCOP102' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP102' These characteristics in combination distinguish 'DANCOP102' as a new and distinct *Sutera* cultivar:

1. Semi-trailing, elongated growth habit.
2. Extra large white flowers.

3. Very well branched with long, strong branches.
4. Early, abundant flowering.
5. Strong plant vigor.

PARENT COMPARISON

Plants of the new cultivar 'DANCOP102' are similar to plants of the seed parent, *Sutera cordata* 'cv. 09-1472' in most horticultural characteristics, however, plants of the new cultivar 'DANCOP102' differ in the following:

1. Semi-trailing, elongated growth habit. Seed parent has a trailing and elongated growth habit.
2. White flowers. Seed parent has light pink flowers.
3. Very branched with long, strong branches. Seed parent has moderate branching.
4. Early, abundant flowering. Seed parent has late, moderate quantity flowering.
5. Strong vigor. Seed parent has medium vigor.

COMMERCIAL COMPARISON

Plants of the new cultivar 'DANCOP102' are comparable to the commercial variety *Sutera* 'DANCOP40' U.S. Plant Pat. No. 23,147. The two *Sutera* varieties are similar in most horticultural characteristics; however, the new variety 'DANCOP102' differs in the following:

1. Comparison variety has compact, mounded growth habit whereas candidate variety has semi-trailing, elongated growth habit.
2. Comparison variety has commercially recognized extra large white flowers, smaller than the even larger flowers of the new variety.
3. Plants of the comparison variety has medium vigor, whereas candidate variety has strong vigor.

Plants of the new cultivar 'DANCOP102' are also comparable to the unpatented commercial variety *Sutera* 'Scopia Great White improved'. The two *Sutera* varieties are similar in most horticultural characteristics; however, the new variety 'DANCOP102' differs in the following:

1. Comparison variety has medium, white flowers whereas candidate variety has double extra large white flowers.
2. Comparison variety is extremely well branched, with more branches than candidate variety.
3. Comparison variety does not bloom as early as candidate variety.
4. Flowering of comparison variety is not as abundant as candidate variety.

BRIEF DESCRIPTION OF THE PHOTOGRAPHS

The accompanying photograph in FIG. 1 illustrates a close up of the flowers.

Figure 2:
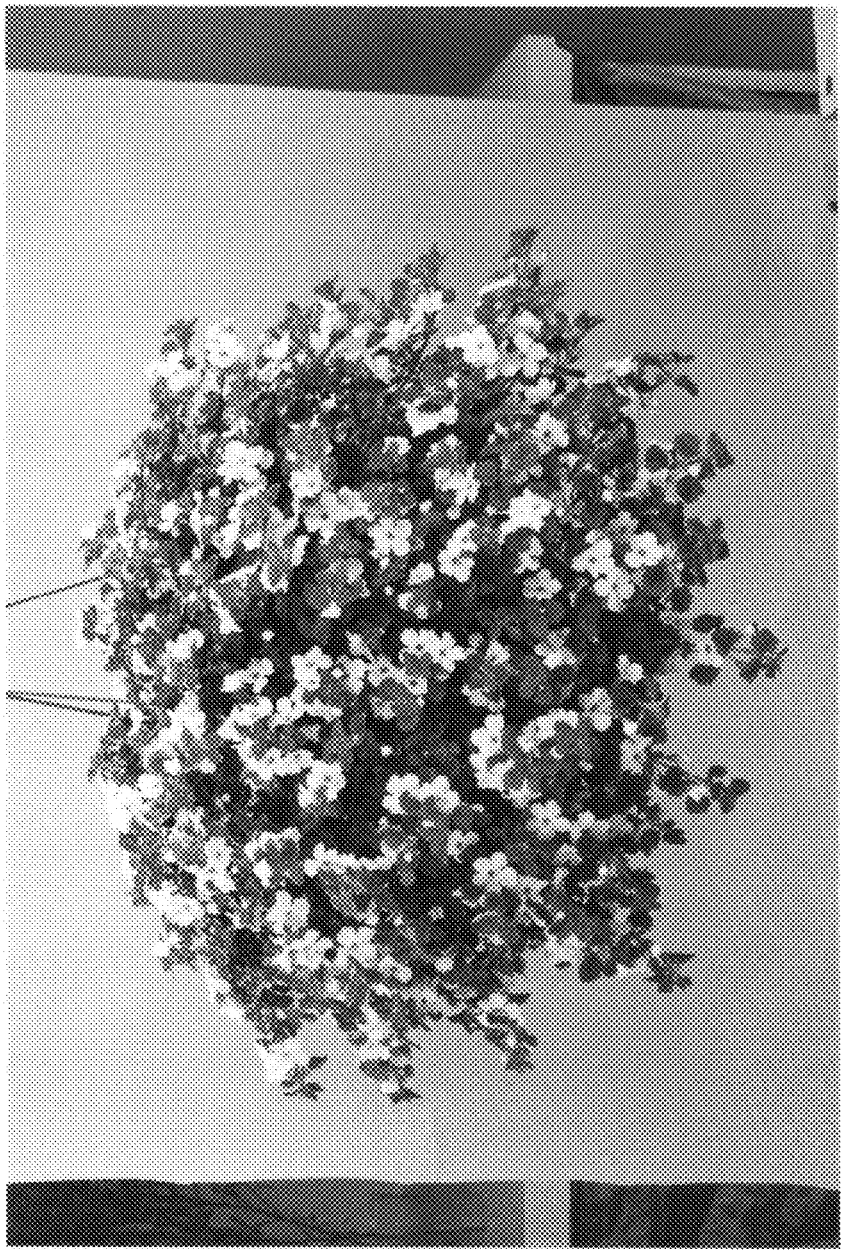

FIG. 2 illustrates in full color a typical plant of 'DANCOP102' grown in a greenhouse, in a 13 cm pot. Age of the plant photographed is approximately 3 months old from rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DANCOP102' plants grown in a greenhouse during Winter to Spring in Moshav Mishmar Hashiva, Israel. The growing temperature ranged from 15° C. to 26° C. during the day and from 13° C. to 16° C. during the night. Measurements and numerical values represent averages of typical plant types.

Botanical classification: *Sutera cordata* 'DANCOP102'.

PROPAGATION

Typical propagation material: Vegetative cuttings.
Time to rooting: 7 to 10 days at approximately 20° C.
Root description: Fine, fibrous roots.

PLANT

Age of plant described: Approximately 3 months old.
Pot size of plant described: 13 cm.
Height: About 12 cm.
Plant spread: About 60 cm.
Growth rate: Medium.
Characteristics of primary lateral branches:
- *Quantity of primary lateral branches*.—About 16.
- *Length of primary lateral branches*.—About 50 cm.
- *Form*.—Cylindrical.
- *Diameter*.—About 0.3 cm.
- *Color*.—RHS Green 147 A.
- *Texture*.—Velvety.
- *Strength*.—Good.

Internode length: About 3 cm.

FOLIAGE

Leaf:
- *Arrangement*.—Opposite, petiolate.
- *Quantity*.—Approximately 60 per branch.
- *Average length*.—3.5 cm.
- *Average width*.—3 cm.
- *Shape of blade*.—Ovate.
- *Apex*.—Obtuse.
- *Base*.—Acuminate.
- *Texture of top surface*.—Velvety.
- *Pubescence*.—Slightly pubescent all surfaces. Velvety.
- *Aspect*.—Flat, angled about 90° to the branch.
- *Color*.—Young foliage upper side: RHS Green 137 B. Young foliage under side: RHS Green 137 C. Mature foliage upper side: RHS Green 147 A. Mature foliage under side: RHS Green 137 A.
- *Venation*.—Type: Pinnate. Venation color upper side: RHS Green 147 A. Venation color under side: RHS Green 137 C.
- *Petiole*.—Length: About 1 cm. Diameter: About 0.3 cm. Color: RHS Green 147 A. Texture: Slightly velvety.

FLOWER

Natural flowering season: All year round.
Days to flowering from rooted cutting: About 45.
Inflorescence and flower type and habit: Axillary, solitary salverform single flowers.
Rate of flower opening: 3 to 5 days from bud to fully opened flower.
Flower longevity on plant: About 7 days.
Persistent or self-cleaning: Persistent.
Bud:
- *Shape*.—Spatulate.
- *Length*.—About 1.7 cm.
- *Diameter*.—About 0.8 cm.
- *Color*.—RHS White 155 C.

Flower size:
- *Diameter*.—About 3.2 cm.
- *Length*.—About 1.8 cm.
- *Corolla tube diameter*.—About 0.5 cm.

Corolla/petals:
- *Arrangement*.—Symmetric.
- *Lobe length*.—About 1.3 cm.
- *Lobe width*.—About 1.2 cm.
- *Quantity*.—5.
- *Texture*.—Velvety.
- *Lobe apex*.—Rounded.
- *Lobe shape*.—Rounded.
- *Margin*.—Entire.
- *Aspect*.—About 90° to the tube.

Color:
- *When opening*.—Upper surface: RHS White 155 C. Lower surface: RHS White 155 C.
- *Fully opened*.—Upper surface: RHS. White 155 C. Lower surface: RHS White 155 C.

Visible corolla tube color: RHS Yellow-Orange 21 A.
Calyx/sepals:
- *Quantity per flower*.—5.
- *Shape*.—Linear.
- *Length*.—About 0.9 cm.
- *Width*.—About 0.1 cm.
- *Apex*.—Acute.
- *Base*.—Fused.
- *Margin*.—Entire.
- *Texture*.—Slightly velvety.
- *Color*.—Upper Surface: RHS Green 137 A. Lower Surface: RHS Green 137 A.

Peduncle: None.
Pedicel:
- *Length*.—Approximately 1.0 cm.
- *Diameter*.—Approximately 0.1 cm.
- *Color*.—Near RHS Green 137 A.
- *Orientation*.—Slanted upward and outward.
- *Pubescence*.—Slightly pubescent.

Fragrance: None.

REPRODUCTIVE ORGANS

Stamens:

*Number*.—4.

*Filament length*.—Approximately 1.2 cm.

Anthers:

*Shape*.—Cylindrical.

*Length*.—Approximately 0.1 cm.

*Color*.—RHS Yellow 13 B.

*Pollen*.—Color: RHS Yellow-Orange 21 B. Quantity: Sparse.

Pistil:

*Number*.—1.

*Length*.—About 1.4 cm.

*Style*.—Length: About 1 cm. Color: RHS Yellow-Green 144 D.

*Stigma*.—Shape: Undulate. Color: RHS Yellow-Green 144 A. Ovary Color: RHS Green 144 C.

OTHER CHARACTERISTICS

Seeds and fruits: About 20 elliptic, small (1 mm long) Beige seeds per one elliptic Brown capsule. Minute seeds, not well measured by R.H.S. chart.

Disease/pest resistance: Neither resistance nor susceptibility to pathogens and pests common to *Sutera* have been observed.

Temperature tolerance: The new variety tolerates temperatures between 5 to 40° C.

What is claimed is:

1. A new and distinct cultivar of *Sutera* plant named 'DANCOP102' as herein illustrated and described.

* * * * *